(12) United States Patent  
Chen et al.

(10) Patent No.: US 9,388,168 B2
(45) Date of Patent: Jul. 12, 2016

(54) PROCESS FOR THE PREPARATION OF 1-([1,3]DIOXOLAN-4-YLMETHYL)-1H-PYRAZOL-3-YLAMINE

(71) Applicant: Hua Medicine, Grand Cayman (KY)

(72) Inventors: Junli Chen, Shanghai (CN); Yi Ren, Shanghai (CN); Jin She, Shanghai (CN); Lin Wang, Shanghai (CN)

(73) Assignee: HUA MEDICINE, Grand Gayman (KY)

( * ) Notice: Subject to any disclaimer, the term of this patent is extended or adjusted under 35 U.S.C. 154(b) by 0 days.

(21) Appl. No.: 14/655,287

(22) PCT Filed: Dec. 20, 2013

(86) PCT No.: PCT/EP2013/077563
§ 371 (c)(1),
(2) Date: Jun. 24, 2015

(87) PCT Pub. No.: WO2014/102164
PCT Pub. Date: Jul. 3, 2014

(65) Prior Publication Data
US 2015/0315176 A1     Nov. 5, 2015

(30) Foreign Application Priority Data

Dec. 25, 2012    (WO) ................ PCT/CN2012/087380

(51) Int. Cl.
*C07D 405/06*     (2006.01)
*C07D 231/40*     (2006.01)
*C07D 403/12*     (2006.01)

(52) U.S. Cl.
CPC ............ *C07D 403/12* (2013.01); *C07D 231/40* (2013.01); *C07D 405/06* (2013.01)

(58) Field of Classification Search
None
See application file for complete search history.

(56) References Cited

U.S. PATENT DOCUMENTS 8,178,689 B2 *    5/2012    Sarabu ............... A61K 31/4155
                                                        546/276.7

FOREIGN PATENT DOCUMENTS

EP          2 236 498 A1    10/2010
WO      2009/127546 A1    10/2009

* cited by examiner

*Primary Examiner* — Kamal Saeed
(74) *Attorney, Agent, or Firm* — McDonnell Boehnen Hulbert & Berghoff LLP

(57) ABSTRACT

The present invention relates to a novel process for the preparation of of the formula (I) (I) wherein $R^1$ and $R^2$ are described herein. The compounds prepared by the present invention are useful in the synthesis and manufacture of compounds for treating diseases or conditions associated with inhibiting actin polymerization.

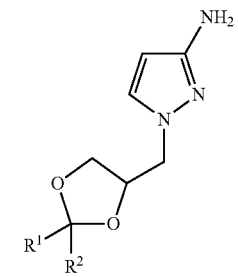

(I)

19 Claims, No Drawings

PROCESS FOR THE PREPARATION OF 1-([1,3]DIOXOLAN-4-YLMETHYL)-1H-PYRAZOL-3-YLAMINE

This application is a US national phase of International Application No. PCT/EP2013/077563 filed on Dec. 20, 2013, which claims priority to International Patent Application No. PCT/CN2012/087380 filed on Dec. 25, 2012.

FIELD OF THE INVENTION

The present invention relates to a process for the preparation of a compound of the formula (I)

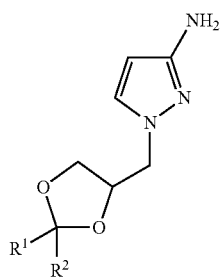

wherein $R^1$ and $R^2$ are independently selected from hydrogen, $C_{1-6}$alkyl, $C_{3-7}$cycloalkyl, $C_{3-6}$alkenyl, or phenyl; wherein $C_{1-6}$alkyl, cycloalkyl, $C_{3-6}$alkenyl or phenyl may optionally be substituted by halogen, hydroxyl, $C_{1-6}$alkoxycarbonyl, or phenyl; or
$R^1$ and $R^2$, together with the carbon to which they are attached, form a $C_{3-7}$cycloalkyl, which are useful in the synthesis and manufacture of pharmaceutical active compounds as described in the U.S. Pat. No. 7,741,327 B2.

BACKGROUND OF THE INVENTION

The U.S. Pat. No. 7,741,327 B2 disclosed various synthetic approaches to the aminopyrazole derivatives of formula (I).

However, it was found that the key intermediate 1-nitropyrazole is a high energy compound and was potentially explosive under reaction conditions. In addition, the overall yield of the above mentioned synthetic approaches were low to moderate based on low yielding reaction steps, formation of several by-products, unselective reactions and incomplete conversions.

One object of the invention therefore is to find an alternative synthetic approach which can be applied on a technical scale and which allows to obtain the product in a higher yield and desired purity and without the need of using unsafe intermediates.

The object could be achieved with the process of the present invention as outlined below.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example as methyl, ethyl, n-propyl, isopropyl, n-butyl, s-butyl, isobutyl, t-butyl, n-pentyl, 3-methylbutyl, n-hexyl, 2-ethylbutyl and the like. Particular "$C_{1-6}$alkyl" groups are methyl and ethyl. More particular "$C_{1-6}$alkyl" group is methyl.

The term "alkoxide" alone or in combination signifies a group alkyl-O⁻, wherein the "alkyl" signifies a saturated, linear- or branched chain alkyl group, for example as methyl, ethyl, n-propyl, isopropyl, n-butyl, s-butyl, isobutyl, t-butyl, n-pentyl, 3-methylbutyl, n-hexyl, 2-ethylbutyl and the like; for example methoxide, ethoxide, propoxide, iso-propoxide, n-butoxide, iso-butoxide, 2-butoxide, tert-butoxide, hexyloxide and the like. Particular "alkoxide" groups are t-butoxide, methoxide and ethoxide and more particularly t-butoxide.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, hexyloxy and the like. Particular "$C_{1-6}$alkoxy" groups are methoxy and ethoxy and more particularly methoxy.

The term "phenyl $C_{1-6}$alkyl" refers to $C_{1-6}$alkyl group as defined above wherein at least one of the hydrogen atoms of the $C_{1-6}$alkyl group is replaced by a phenyl group. Examples of particular phenyl$C_{1-6}$alkyl groups are benzyl, 4-methylbenzyl, 4-fluorobenzyl, 3-methoxybenzyl, 4-methoxybenzyl, 2-phenylethyl and 3-phenylpropyl. More particular phenyl$C_{1-6}$alkyl group is benzyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclopentyl and cyclohexyl.

The term "carboxy" alone or in combination refers to the group —COOH.

The term "cyano" alone or in combination refers to the group —CN.

The term "halogen" means fluorine, chlorine, bromine or iodine. Halogen is particularly fluorine, chlorine or bromine.

The term "hydroxy" alone or in combination refers to the group —OH.

The term "carbonyl" alone or in combination refers to the group —C(O)—.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

In detail, the present invention is directed to a process for the preparation of a compound of the formula (I)

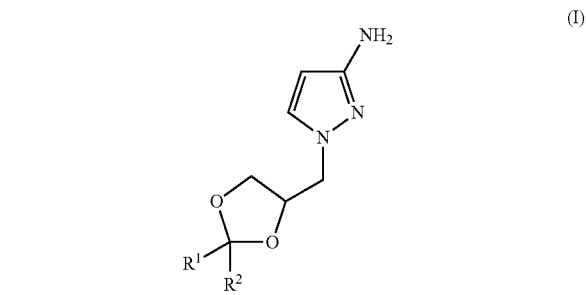

wherein $R^1$ and $R^2$ are independently selected from hydrogen, $C_{1-6}$alkyl, $C_{3-7}$cycloalkyl, $C_{3-6}$alkenyl, or phenyl; wherein $C_{1-6}$alkyl, cycloalkyl, $C_{3-6}$alkenyl or phenyl may optionally be substituted by halogen, hydroxyl, $C_{1-6}$alkoxycarbonyl, or phenyl; or $R^1$ and $R^2$, together with the carbon to which they are attached, form a $C_{3-7}$cycloalkyl; comprising the following steps a) protection of 3-aminopyrazole to form a compound of formula (II);

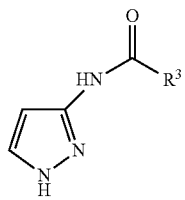
(II)

wherein $R^3$ is $C_{1-6}$alkyl, cycloalkyl or phenyl;

b) 1-substitution of the protected 3-aminopyrazole of the formula (II) to form a compound of formula (III);

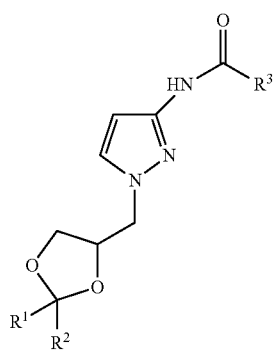
(III)

c) hydrolysis of the protected 3-aminopyrazole of formula (III) under basic conditions to form a compound of formula (I);

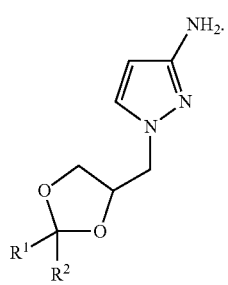
(I)

The present invention relates particularly to a process for the preparation of a compound of formula (Ia)

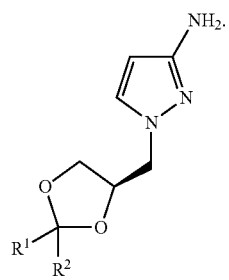
(Ia)

The present invention further relates to a process for the preparation of 1-((R)2,2-dimethyl-[1,3]dioxolan-4-ylmethyl)-1H-pyrazol-3-ylamine

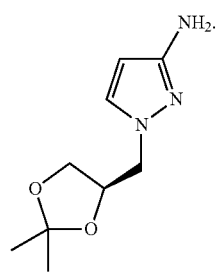

Step a)

Step a) relates to the protection of 3-aminopyrazole to form a compound of the formula (II)

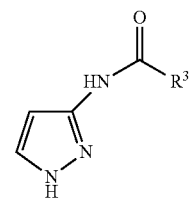
(II)

and in particular the reaction is performed with a carboxylating agent at a reaction temperature between 20 and 100° C.

A suitable solvent system and 3-aminopyrazole are charged to a reaction vessel. The order of addition can be compelled by convenience, or by other process issues familiar to a person skilled in the art.

While the reaction can be conducted in numerous non-alcoholic solvents, in particular, the reaction is performed in a solvent selected from tetrahydrofuran, acetic acid, water, iso-propyl acetate or ethyl acetate. More particular solvent is ethyl acetate.

The charging of 3-aminopyrazole and the appropriate solvent is followed by the addition of a carboxylating agent. In a particular embodiment, the carboxylating agent in step a) is acetic anhydride, acetyl chloride, benzoic anhydride, benzoyl chloride or pivaloyl chloride. More particular carboxylating agent is acetic anhydride.

The amount of carboxylating agent is typically based on the molar equivalents of 3-aminopyrazole and in particular is 1.0-2.0 molar equivalents.

In particular, the reaction temperature is between 40 to 80° C. More particular reaction temperature is 60° C.

After an appropriate amount of time, usually 1-6 hours, the reaction is in particular monitored by HPLC. The amide of formula (II) can be isolated by methods known to the skilled in the art such as by filtration. The product is dried under vacuum, and in particular at a temperature in the range 30 to 60° C., to constant weight.

In particular, the protection of the 3-aminopyrazole is done with a protecting group which can be deprotected under non-acidic conditions, more particularly under basic conditions. Such protecting groups are known to the man skilled in the art.

Step b)

Step b) comprises the alkylation of a compound of formula (II) to the formation of a compound of formula (III) and the reaction is performed with an alkylation agent in an organic solvent with a base and a lithium salt additive at temperature of 70 to 150° C.

A compound of formula (II) and a suitable solvent system are charged to a vessel. The order of addition can be compelled by convenience, or by other process issues familiar to chemistry person skilled in the art.

While the reaction can be conducted in many organic solvents. In a particular embodiment, solvent used in step b) is dimethylformamide, dimethylacetamide, N-methylpyrrolidinone or dimethylsulfoxide. And more particular solvent is dimethylformamide.

The charging of the formula (II) compound and the appropriate solvent is followed by the addition of a base. Particular base is step b) is sodium, lithium, or potassium salts of alkoxide. More particular base is sodium tert-butoxide. The amount of base is typically based on the molar equivalents of formula (II), and in particular is 1.0-3.0 molar equivalents.

Following the charging of the base, a lithium salt was added. Particular lithium salt used in step b) is lithium chloride, lithium bromide or lithium iodide. Particular lithium salt is lithium chloride. The amount of lithium salt is typically based on the molar equivalents of formula (II), and is in particular 0.5-3.0 molar equivalents, and more particular 1.0-1.5 equivalents.

To above mixture was added alkylation agent which is the oxanane derivative. In a particular embodiment, the alkylation agent is

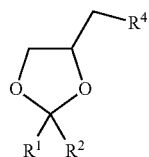

wherein $R^1$ and $R^2$ are defined as above; and
$R^4$ is chloro, bromo, iodo or —O—SO$_2$—R$^5$, wherein $R^5$ is $C_{1-6}$alkyl, phenyl or phenyl substituted by one to three substituents independently selected from $C_{1-6}$alkyl, halogen or nitro.

More particular alkylation agent is

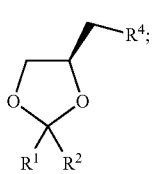

Wherein $R^1$, $R^2$ and $R^4$ are defined as above.

A further particular alkylation agent is

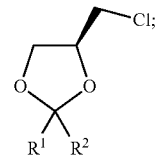

wherein $R^1$ and $R^2$ are defined as above.

The formation of a compound of formula (III) is particularly done between 70 to 150° C. And a more particular reaction temperature in step b) is between 90 and 110° C.

The reaction can be monitored by HPLC. Depending on the starting solvents and temperature, the reaction is generally complete in 3-24 hours, and addition of extra base and the oxanane derivative may be required. After removal of the organic reaction solvent by distillation, the reaction can be quenched by the addition of water. The product of formula (III) can be extracted using an organic solvent, such as ethyl acetate, iso-propyl acetate, 2-methyl-tetrahydrofuran, or dichloromethane. Particular extraction solvent is dichloromethane. The product can be crystallized and isolated by filtration, or after removal of the extraction solvent, the crude product of formula (III) can be used directly in step c).

A compound of formula (III)

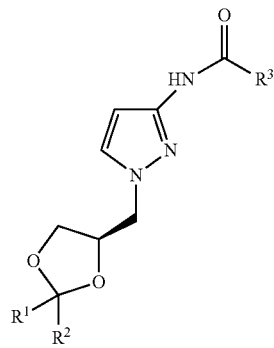

wherein $R^1$ is methyl, $R^2$ is methyl and $R^3$ is methyl.

Step c)

Step c) comprises hydrolysis of the 1-alkylated 3-aminopyrazole amide of formula (III) to form a compound of formula (I). Step c) is performed in solvent with a base at a temperature of 40 to 100° C.

A compound of formula (III) and a suitable solvent system are charged to a vessel. The order of addition can be compelled by convenience, or by other process issues familiar to a person skilled in the art.

While the reaction can be conducted in many organic solvents; particular solvent used in step c) is methanol, ethanol or water. or a mixture thereof. More particular solvent is water.

The charging of the formula (II) compound and the appropriate solvent is followed by the addition of a base. In a particular embodiment, the base used in step c) is sodium hydroxide, lithium hydroxide or potassium hydroxide, in a more particular embodiment, the base is sodium hydroxide.

The amount of base is typically based on the molar equivalents of formula (III), and is in particular 3-6 molar equivalents. The formation of a compound of formula (I) is in particular done between 40 to 100° C. In a more particular embodiment, the reaction temperature of step c) is between 60 to 80° C.

The reaction can be monitored by HPLC. Depending on the starting solvents and temperature, the reaction is generally complete in 8-48 hours.

The present invention also encompasses a process as defined above comprising steps a), b) and c) and further comprising the following steps d) the reaction of a compound of formula (Ia) with a compound of formula (IV) to give a compound of formula (V)

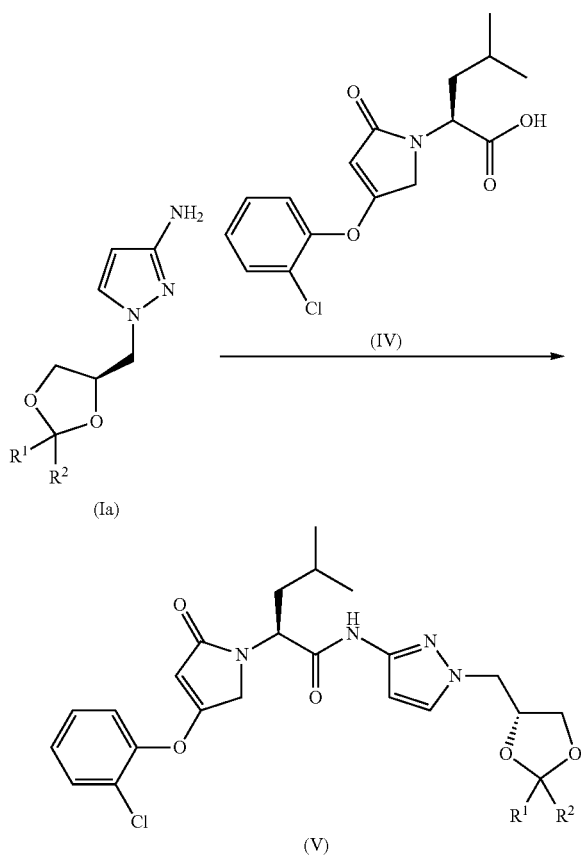

and e) the deprotection of the compound of formula (V) to give (S)-2-[4-(2-Chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

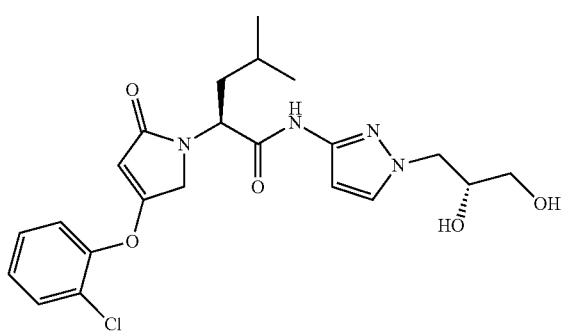 [SMILES: CC(C)C[C@@H](C(=O)Nc1ccn(C[C@@H](O)CO)n1)N1CC(Oc2ccccc2Cl)=CC1=O]

Step d)

Step d) comprises amide coupling of compound of formula (Ia) and a compound of formula (IV) to form a compound of formula (V). Step d) is performed in solvent with an amide coupling reagent and a catalyst at a temperature of −10 to 25° C.

A compound of formula (IV), a compound of formula (Ia), and a suitable solvent system are charged to a vessel. The order of addition can be compelled by convenience, or by other process issues familiar to a person skilled in the art.

While the reaction can be conducted in many organic solvents; particular solvent used in step d) is methylene chloride.

To above mixture was added an amide coupling reagent and a catalyst. In a particular embodiment, the amide coupling reagent used in step d) is 1-(3-dimethylaminopropyl)-3-ethylcarbodiimide, and the catalyst used in step d) is 1-hydroxybenzotriazole.

The amount of the compound of formula (Ia) is typically based on the molar equivalents of formula (IV) and is in particular 1.0-2.0 molar equivalents. The amount of amide coupling reagent is typically based on the molar equivalents of formula (IV) and is in particular 1.0-3.0 molar equivalents. The amount of catalyst is typically based on the molar equivalents of formula (IV) and is in particular 0.05-1.1 molar equivalents.

The formation of a compound of formula (V) is in particular done between −10 to 25° C. In a more particular embodiment, the reaction temperature of step c) is between 0 to 15° C.

The reaction can be monitored by HPLC. Depending on the reaction temperature, the reaction is generally complete in 1-24 hours. The reaction can be quenched by the addition of water. After removal of the aqueous phase, the organic reaction solvent was removed by distillation. The amide of formula (V) can be isolated by methods known to the skilled in the art such as by filtration. The product is dried under vacuum, and in particular at a temperature in the range 30 to 60° C., to constant weight.

Step e)

Step e) comprises removal of a ketal protecting group from a compound of formula (V) to form (S)-2-[4-(2-Chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide. Step e) is performed in solvent with an acid at a temperature of 0 to 40° C.

A compound of formula (V) and a suitable solvent system are charged to a vessel. The order of addition can be compelled by convenience, or by other process issues familiar to a person skilled in the art.

While the reaction can be conducted in many organic solvents; particular solvents used in step d) are ethanol, 2-propanol, tetrahydrofuran, and 2-methyltetrahydrofuran. More particular solvent is 2-propanol.

To above mixture was added an acid. In a particular embodiment, the acid used in step d) is aqueous HCl, and the concentration is 1.0-6.0N.

The amount of the acid is typically based on the molar equivalents of formula (V) and is in particular 1-10 molar equivalents.

The formation of (S)-2-[4-(2-Chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide is in particular done between 0 to 40° C. In a more particular embodiment, the reaction temperature of step e) is between 15 to 25° C.

The reaction can be monitored by HPLC. Depending on the reaction temperature, the reaction is generally complete in 1-24 hours. The reaction can be quenched by the addition of water. The product can be extracted using an organic solvent, such as ethyl acetate, iso-propyl acetate, 2-methyl-tetrahydrofuran, or methyl tert-butyl ether. Particular extraction solvent is methyl tert-butyl ether. After removal of the organic solvent by distillation, the product can be diluted with ethanol and used directly for drug product manufacturing.

The invention is illustrated further by the following examples that are not to be construed as limiting the invention in scope to the specific procedures described in them.

EXAMPLES

Example 1

Preparation of N-(1H-pyrazol-3-yl)-acetamide

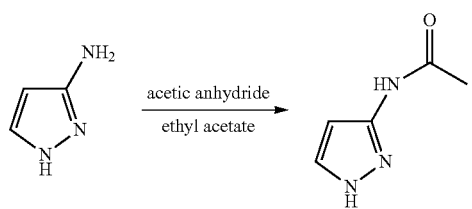

To a 2 L glass flask was charged with 200 g (2.36 mol) of 3-aminopyrazole and 900 g of ethyl acetate. The mixture was agitated at 45° C. for 30 min to form a homogeneous solution. To the mixture was added 245 g (2.36 mol) of acetic anhydride over 1.2 h. The mixture was stirred at 60° C. for 3 h. HPLC analysis of reaction mixture indicated the presence of 3-aminopyrazole. Another 9.7 g (0.09 mol) of acetic anhydride was added into the mixture over 15 min at ca. 60° C. The resulting suspension was agitated for another 2 h at ca. 60° C. The mixture was cooled to 20-25° C. and stirred at that temperature for 15 h. The solids were collected by filtration and washed with 630 g of ethyl acetate. The solids were dried in a vacuum oven (45-50° C./P≤–0.1 MPa) for ca. 24 h to afford 295.2 g (94% yield) of N-(1H-pyrazol-3-yl)-acetamide as off-white solid. $^1$H-NMR (400 MHz, d6-DMSO): δ 12.26 (s, 1H), 10.33 (s, 1H), 7.57 (s, 1H), 6.47 (s, 1H), 1.99 (s, 3H).

Example 2

Preparation of N-[1-((R)-2,2-Dimethyl-[1,3]dioxolan-4-ylmethyl)-1H-pyrazol-3-yl]-acetamide

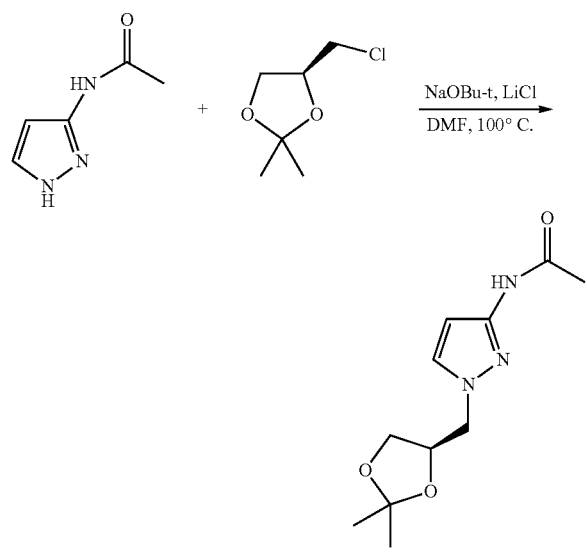

A 3 L flask was charged with 200.0 g (1.60 mol) of N-(1H-pyrazol-3-yl)-acetamide and 1 L of anhydrous DMF. To the agitated suspension was added 173.8 g (1.75 mol) of sodium tert-butoxide in one portion. To the mixture was added 82.0 g (1.91 mol) of lithium chloride in one portion. To the mixture was added 267 g (1.75 mol) of (S)-(–)-4-(chloromethyl)-2,2-dimethyl-1,3-dimethyl-1,3-dioxolane in one portion. The mixture was agitated at 100° C. for 5 h. To the resulted mixture was added additional 31.6 g (0.32 mol) of sodium tert-butoxide and followed by 48.5 g (0.32 mol) of (S)-(–)-4-(chloromethyl)-2,2-dimethyl-1,3-dimethyl-1,3-dioxolane. The mixture was agitated at 100° C. for additional 5 h. To the resulted mixture was added additional 31.6 g (0.32 mol) of sodium tert-butoxide and followed by 48.5 g (0.32 mol) of (S)-(–)-4-(chloromethyl)-2,2-dimethyl-1,3-dimethyl-1,3-dioxolane. The mixture was agitated at 100° C. for 16 h. Then the mixture was cooled to 60° C. and concentrated under reduced pressure (60-25 mbar, 60° C.) to remove 720 g of the solvents. To the residue was added 1.6 L of water. The resulting solution was extracted with 3.2 L of dichloromethane (DCM). The combined organic phases were washed with 1.6 L of 20 wt % sodium chloride solution, and concentrated by distillation in vacuo (30-40° C. (batch)/P<–100 mbar), giving 585 g (316 g after corrected with wt %, 82.8% yield) of N-[1-((R)-2,2-Dimethyl-[1,3]dioxolan-4-ylmethyl)-1H-pyrazol-3-yl]-acetamide as a red-brown oil which was used in the subsequent step directly without further processing. $^1$H-NMR (400 MHz, d6-DMSO): δ 10.37 (s, 1H), 7.57 (s, 1H), 6.44 (s, 1H), 4.33-4.36 (m, 1H), 4.08-4.11 (m, 2H), 3.98-4.02 (m, 1H), 3.71-3.75 (m, 1H), 1.98 (s, 3H), 1.31 (s, 3H), 1.26 (s, 3H).

Example 3

Preparation of 1-((R)-2,2-Dimethyl-[1,3]dioxolan-4-ylmethyl)-1H-pyrazol-3-ylamine

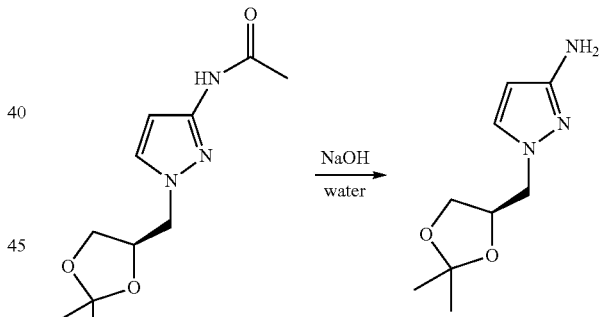

To a 5 L glass flask equipped with a mechanical stirrer and thermometer was charged with 584 g (315 g after corrected by wt %, 1.28 mol) of N-[1-((R)-2,2-Dimethyl-[1,3]dioxolan-4-ylmethyl)-1H-pyrazol-3-yl]-acetamide and 1.2 L of purified water. The mixture was agitated at 60-65° C. for 3 h, forming a homogeneous solution. After cooling the batch to 40-45° C., 214 g (5.14 mol) of NaOH (solid) was added in portions. The mixture was agitated at 90° C. for 24 h. The mixture was cooled to 20-25° C. and extracted with 2 kg of isopropyl acetate. The combined organic phase was concentrated by distillation in vacuo (35-45° C. (batch)/P<–0.1 MPa) to give a yellow oil. The residue was diluted with 414 g of methyl tert-butyl ether and 750 g of heptane subsequently. The resulting suspension was stirred at 20-25° C. for 15 h. The solids were collected by filtration and washed with 1100 g of methyl tert-butyl ether/heptane (1/2, v/v). The solids were dried in a vacuum oven (30-35° C./P≤–0.1 MPa) for ca. 24 h to afford 215 g (68% yield in 2 steps) of 1-((R)-2,2-Dimethyl-[1,3]

dioxolan-4-ylmethyl)-1H-pyrazol-3-ylamine as an off-white solid. ¹H-NMR (400 MHz, d6-DMSO): δ 7.31 (s, 1H), 5.38 (s, 1H), 4.55 (s, 2H), 4.26-4.32 (m, 1H), 3.92-3.98 (m, 3H), 3.7-3.73 (m, 1H), 1.31 (s, 3H), 1.25 (s, 3H).

Example 4

Preparation of N-(1H-pyrazol-3-yl)-benzamide

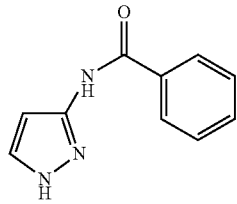 [SMILES: O=C(Nc1cc[nH]n1)c1ccccc1]

3-Aminopyrazole (9 g, 108 mmol) was dissolved in DCM (250 ml). N-methylmorpholine (26.5 g, 262 mmol) was added in one portion. Benzoyl chloride (34.86 g, 248 mmol) was added slowly at room temperature. After stirring at room temperature for 16 hours, the mixture was concentrated under reduced pressure to give a solid. The solid was dissolved in methanol (200 ml). Aqueous solution of NaOH (2.5M, 120 ml, 300 mmol) was added slowly, and THF (50 ml) was added in order to obtain a homogeneous solution. After stirring at room temperature for 20 minutes, the mixture was concentrated under reduced pressure and poured into water (300 ml). The precipitate was filtered and dried in an oven to afford 17.55 g light yellow solid, the yield was 87.7%. ¹H-NMR (400 MHz, d6-DMSO): δ 12.45 (s, 1H), 10.79 (s, 1H), 7.99-8.02 (m, 2H), 7.67 (s, 1H), 7.48-7.59 (m, 3H), 6.65 (s, 1H).

Example 5

Preparation of N-[1-((R)-2,2-Dimethyl-[1,3]dioxolan-4-ylmethyl)-1H-pyrazol-3-yl]-benzamide

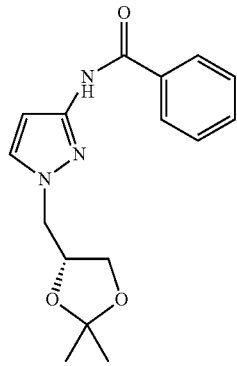 [SMILES: CC1(C)OC[C@@H](Cn2ccc(NC(=O)c3ccccc3)n2)O1]

N-(1H-Pyrazol-3-yl)-benzamide (2.5 g, 20 mmol) and 4-Chloro-benzenesulfonic acid 2,2-dimethyl-[1,3]dioxolan-4-ylmethyl ester (6.75 g, 22 mmol) were dissolved in anhydrous 1,4-dioxane (30 ml). Sodium tert-butoxide (2.28 g, 23.8 mmol) was added in one portion at room temperature. The yellow suspension was heated to reflux with agitation for 23 hrs. The mixture was cooled to 10° C., water (80 ml) was added. The mixture was extracted with ethyl acetate (30 ml*2), the organic layer was washed with 1N NaOH (20 ml), 10% aqueous NaCl (40 ml*2). The organic layer was dried over Na₂SO₄, concentrated under reduced pressure to give the crude product as oil. Purified by silicon column (hexane/EA=5:1 to hexane/EA=3:1) to give off-white solid (3 g), yield: 50%. ¹H-NMR (400 MHz, d6-DMSO): δ 10.86 (s, 1H), 7.99-8.01 (d, 2H), 7.67 (s, 1H), 7.47-7.58 (m, 3H), 6.63 (s, 1H), 4.4-4.42 (m, 1H), 4.16-4.38 (m, 2H), 4.01-4.05 (m, 1H), 3.75-3.78 (m, 1H), 1.33 (s, 3H), 1.25 (s, 3H).

Example 6

Preparation of 1-((R)-2,2-Dimethyl-[1,3]dioxolan-4-ylmethyl)-1H-pyrazol-3-ylamine

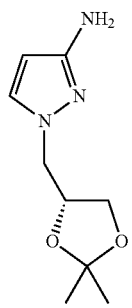

N-[1-((R)-2,2-Dimethyl-[1,3]dioxolan-4-ylmethyl)-1H-pyrazol-3-yl]-benzamide (150 mg, 0.5 mmol) was dissolved in methanol (2 ml), and water (1 ml) was added in one portion. The mixture was stirred at room temperature for 30 minutes. NaOH (120 mg, 3 mmol) was added. The mixture was stirred at reflux for 18 h. UPLC indicated the conversion was ~20%, so the mixture was agitated for another 20 h. The conversation was still ~40%. Another portion of NaOH (120 mg, 3 mmol) was added into the mixture. The mixture was agitated at reflux for another 20 h. The conversation was ~70%. No further workup.

Example 7

Preparation of 2,2-dimethyl-N-(1H-pyrazol-3-yl)-propionamide

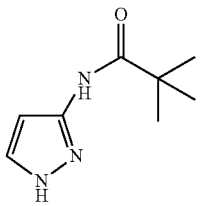

3-Aminopyrazole (9 g, 108 mmol) was dissolved in DCM (250 ml). Triethylamine (27 g, 262 mmol) was added in one portion. Pivaloyl chloride (30 g, 248 mmol) was added slowly at room temperature. After stirring at room temperature for 6 hours, the solvent was concentrated under reduced pressure to give a solid. The solid was dissolved in methanol (200 ml). Aqueous NaOH (2.5M, 120 ml) was added slowly and the mixture was stirred at room temperature for 30 minutes. The solvent was evaporated off under reduced pressure. The slurry was transferred into water (300 ml). The solid was filtrated and dried to give the title product (13.5 g) as a yellow solid, yield: 76%. ¹H-NMR (400 MHz, d6-DMSO): δ 12.3 (s, 1H), 9.77 (s, 1H), 7.58 (s, 1H), 6.49 (s, 1H), 1.2 (s, 9H).

Example 8

Preparation of N-[1-((R)-2,2-dimethyl-[1,3]dioxolan-4-ylmethyl)-1H-pyrazol-3-yl]-2,2-dimethyl-propionamide

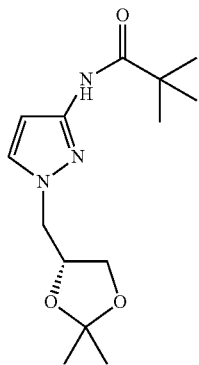 [SMILES: CC1(C)OC[C@@H](Cn2ccc(NC(=O)C(C)(C)C)n2)O1]

2,2-Dimethyl-N-(1H-pyrazol-3-yl)-propionamide (1.67 g, 10 mmol) was dissolved in DMF (17 ml). (S)-4-Chloromethyl-2,2-dimethyl-[1,3]dioxolane (1.52 g, 10 mmol) was added into the mixture. Finally Sodium tert-butoxide (0.98 g, 10 mmol) was added at room temperature. The mixture was heated to 100° C. with agitation for 23 hours under $N_2$ atmosphere. UPLC indicated that there was 26% 2,2-Dimethyl-N-(1H-pyrazol-3-yl)-propionamide remained in the mixture. Additional 2,2-Dimethyl-N-(1H-pyrazol-3-yl)-propionamide (0.76 g, 5 mmol) and Sodium tert-butoxide (0.49 g, 5 mmol) was added. The mixture was stirred at 100° C. for another 24 hrs. HPLC indicated 2,2-Dimethyl-N-(1H-pyrazol-3-yl)-propionamide was 9.4% remained, the selectivity of N1/N2 alkylation products was 2.8:1. The DMF was concentrated under reduced pressure. Water (10 ml) was added. The mixture was extracted with DCM (2×12 ml), the organic layer was washed with 10% aqueous NaCl (2×20 ml). The organic layer was dried over $Na_2SO_4$, concentrated under reduced pressure to give oil, which is purified by silicon column (hexane/EA=5:1 to hexane/EA=3:1) to give off-white solid (0.84 g), yield: 30%. $^1$H-NMR (400 MHz, d6-DMSO): δ 9.85 (s, 1H), 7.59 (s, 1H), 6.47 (s, 1H), 4.36-4.39 (m, 1H), 4.08-4.12 (m, 2H), 4.0-4.02 (m, 1H), 3.73-3.75 (m, 1H), 1.33 (s, 3H), 1.26 (s, 3H), 1.19 (s, 9H).

Preparation of 1-((R)-2,2-Dimethyl-[1,3]dioxolan-4-ylmethyl)-1H-pyrazol-3-ylamine

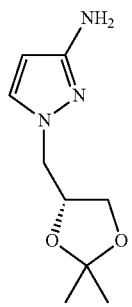

N-[1-((R)-2,2-Dimethyl-[1,3]dioxolan-4-ylmethyl)-1H-pyrazol-3-yl]-2,2-dimethyl-propionamide (1.42 g, 5 mmol) was dissolved in methanol (15 ml), and water (3 ml) was added in one portion. NaOH (1.67 g, 40 mmol) was added in one portion. The mixture was stirred at 70° C. for 40 h. HPLC indicated the conversation was 2.8%. No further workup.

Example 9

Preparation of (S)-2-[4-(2-Chloro-phenoxy)-2-oxo-2,5-dihydro-pyrrol-1-yl]-4-methyl-pentanoic acid [1-((R)-2,2-dimethyl-[1,3]dioxolan-4-ylmethyl)-1H-pyrazol-3-yl]-amide

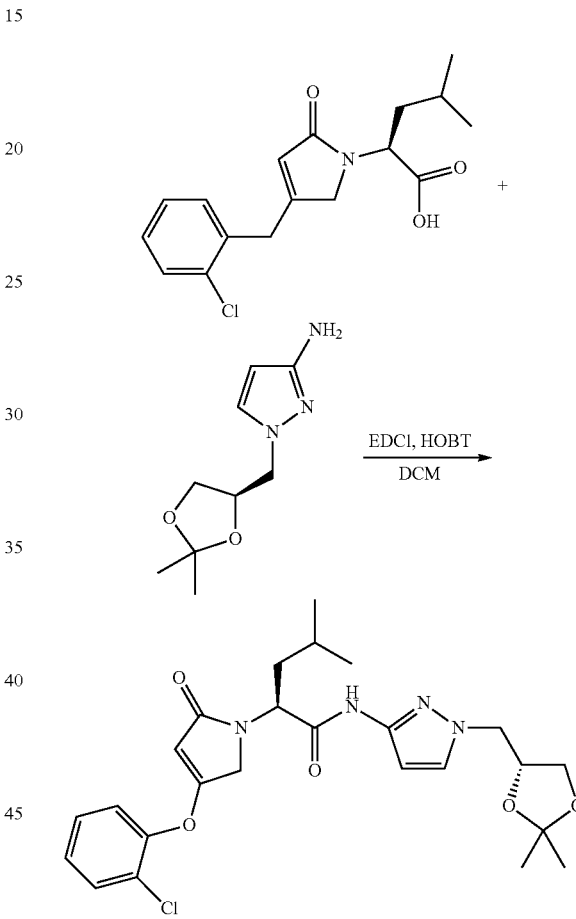

To a 200-L glass-lined reactor was charged with 46.3 kg of dichloromethane (DCM). To the reactor was added additional 112.0 kg of dichloromethane followed by 11.9 kg (36.8 mol) of (S)-2-[4-(2-chloro-phenoxy)-2-oxo-2,5-dihydro-pyrrol-1-yl]-4-methylpentanoic acid and 8.0 kg (40.6 mol) of 1-((R)-2,2-dimethyl-[1,3]dioxolan-4-ylmethyl)-1H-pyrazol-3-ylamine. With agitation, to the mixture was added 0.44 kg of 1-hydroxybenzotriazole. After cooling to 4° C., 14.0 kg of 1-(3-dimethylaminopropyl)-3-ethylcarbodiimide was added in 4 portions (5.0 kg+3.1 kg+3.8 kg+2.1 kg) over 3 h while maintaining the batch temperature at 4-10° C. The mixture was agitated at 4-12° C. for additional 5 h. HPLC analysis at 2.5 h indicated the completion of the reaction. The mixture was transferred into a 500 L glass-line reactor. After adjusting the batch temperature to below 10° C., the reaction was quenched by adding 119.0 kg of water. The aqueous phase was separated and the organic solvent was removed by distillation in vacuo to a final volume of ca. 30 L. To the residue was added 106.0 kg of ethyl acetate. The mixture was stirred for 30 min, cooled to 0-10° C., and washed with 5 wt % citric acid solution, 10 wt % sodium carbonate solution and 2.5 wt % sodium chloride solution. The solvent was removed by distillation in vacuo at 18-30° C. to a final volume of ca. 30 L. To the residue solution was added 64.7 kg of n-heptane over 2.5 h. After adjusting the batch temperature to 0-5° C. the mixture was agitated for 4.5 h. The solids were collected in a Nutsche filter, rinsed with 16.2 kg of n-heptane, dried with nitrogen flow at 40-45° C. for 20 h to afford 17.2 kg (88.1% yield) of ((S)-2-[4-(2-Chlorophenoxy)-2-oxo-2,5-dihydro-pyrrol-1-yl]-4-methyl-pentanoic acid [1-((R)-2,2-dimethyl-[1,3]dioxolan-4-ylmethyl)-1H-pyrazol-3-yl]-amide. $^1$H NMR (300 MHz, DMSO-d6, ethanol removed) δ ppm 0.90 (d, J=6.4 Hz, 3 H), 0.94 (d, J=6.4 Hz, 3 H), 1.05 (br. s., 3 H), 1.06 (br. s., 3 H), 1.36-1.64 (m, 2 H), 1.68-1.84 (m, 1 H), 3.89 (s, 2 H), 4.20 (d, J=18.4 Hz, 1 H), 4.62 (d, J=18.4 Hz, 1 H), 4.68 (s, 1 H), 4.78 (s, 1 H), 4.90 (dd, J=10.7, 4.7 Hz, 1 H), 6.44 (d, J=2.1 Hz, 1 H), 7.37 (td, J=7.8, 1.8 Hz, 1 H), 7.46 (td, J=7.8, 1.2 Hz, 1 H), 7.50-7.56 (m, 2 H), 7.66 (dd, J=7.8, 1.2 Hz, 1 H), 10.81 (s, 1 H).

Example 10

Preparation of (S)-2-[4-(2-Chloro-phenoxy)-2-oxo-2,5-dihydro-pyrrol-1-yl]-4-methyl-pentanoic acid [1-((R)-2,3-dihydroxy-propyl-1H-pyrazol-3-yl]-amide

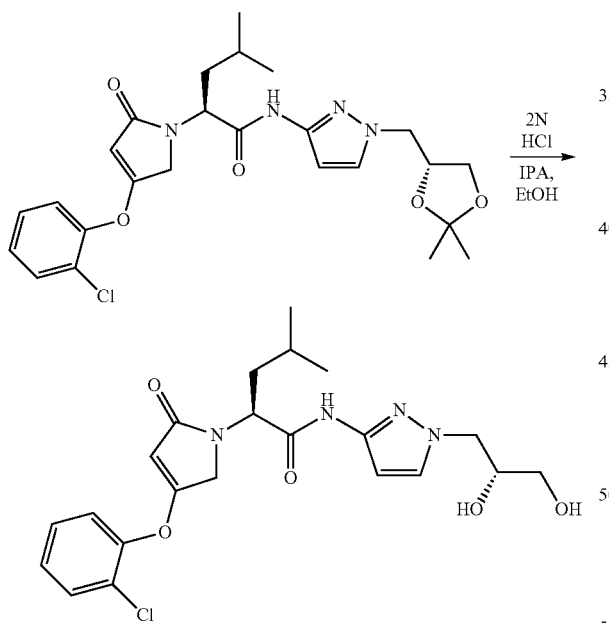

To a 200-L glass-lined reactor was charged with 42.7 kg of 2-propanol and 13.6 kg (27.0 mol) of ((S)-2-[4-(2-Chlorophenoxy)-2-oxo-2,5-dihydro-pyrrol-1-yl]-4-methyl-pentanoic acid [1-((R)-2,2-dimethyl-[1,3]dioxolan-4-ylmethyl)-1H-pyrazol-3-yl]-amide. The suspension was stirred at 25-30° C. until the solids dissolved. After adjusting the batch temperature to <15° C., 59.5 kg of 2.0N hydrochloric acid was added over 3.5 h while maintaining a batch temperature of 9-17° C. The mixture was warmed to 18 to 23° C. and stirred for 5.5 h. HPLC analysis at 2 h indicated the reaction was complete. The reaction mixture was transferred into a 500 L glass-lined reactor and diluted with 28.6 kg of purified water and 166.1 kg of methyl tert-butyl ether. The aqueous phase was separated and the organic phase was washed with 1.0N sodium hydroxide solution, 10.7 wt % sodium chloride solution, and 1.0 wt % sodium chloride solution subsequently. The organic phase was transferred into a 200 L glass-line reactor. Solvents were removed by distillation in vacuo at 10-26° C. to a volume of ca. 27 L. The resulting oil was diluted with 107.6 kg of ethanol and solvents were removed by distillation in vacuo at 12-30° C. to afford 19.85 kg (10.04 kg corrected by wt %, 80.4% of yield) of (S)-2-[4-(2-Chloro-phenoxy)-2-oxo-2,5-dihydro-pyrrol-1-yl]-4-methyl-pentanoic acid [1-((R)-2,3-dihydroxy-propyl-1H-pyrazol-3-yl]-amide in ethanol. $^1$H NMR (300 MHz, DMSO-d6) δ ppm 0.90 (d, J=6.3 Hz, 3 H), 0.94 (d, J=6.3 Hz, 3 H), 1.33-1.50 (m, 1 H), 1.49-1.67 (m, 1 H), 1.68-1.85 (m, 1 H), 3.16-3.32 (m, 2 H), 3.70-3.93 (m, 2 H), 4.09 (m, J=13.6, 3.6 Hz, 1H), 4.21 (d, J=18.4 Hz, 1H), 4.61 (d, J=18.4 Hz, 1 H), 4.71 (t, J=5.6 Hz, 1 H), 4.79 (s, 1 H), 4.88 (dd, J=10.6, 4.8 Hz, 1 H), 4.94 (d, J=5.1 Hz, 1 H), 6.41 (d, J=1.5 Hz, 1 H), 7.37 (t, J=7.5 Hz, 1 H), 7.46 (t, J=7.5 Hz, 1 H), 7.50-7.56 (m, 2 H), 7.65 (d, J=7.5 Hz, 1 H), 10.78 (s, 1 H).

The invention claimed is:

1. A process for the preparation of a compound of the formula

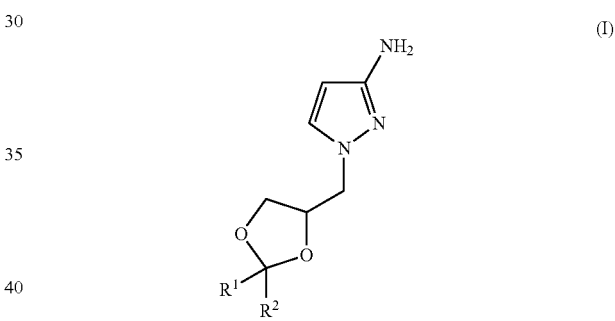

wherein $R^1$ and $R^2$ are independently selected from hydrogen, $C_{1-6}$alkyl, $C_{3-7}$cycloalkyl, $C_{3-6}$alkenyl, or phenyl; wherein $C_{1-6}$alkyl, cycloalkyl, $C_{3-6}$alkenyl or phenyl is optionally be substituted by halogen, hydroxyl, $C_{1-6}$alkoxycarbonyl, or phenyl; or $R^1$ and $R^2$, together with the carbon to which they are attached, form a $C_{3-7}$cycloalkyl;

comprising a) protecting 3-aminopyrazole to form a compound of formula (II);

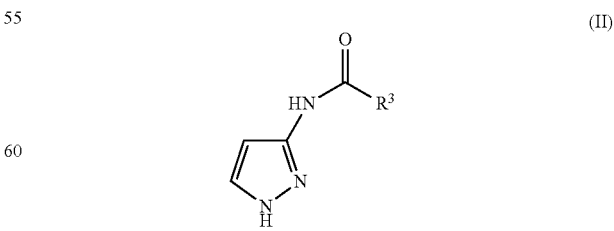

wherein $R^3$ is $C_{1-6}$alkyl, cycloalkyl or phenyl;

b) substituting the protected 3-aminopyrazole of formula (II) at the 1 position to form a compound of formula (III)

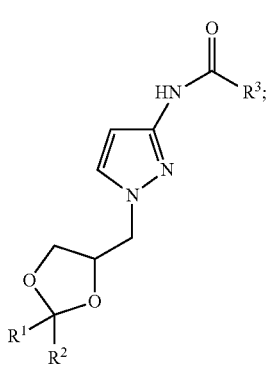
(III)

c) hydrolyzing the protected 3-aminopyrazole of formula (III) under basic conditions to form a compound of formula (I)

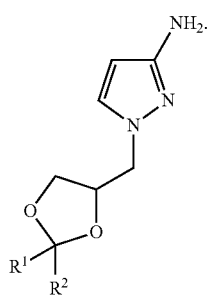
(I)

2. The process according to claim 1, for the preparation of a compound of formula (Ia)

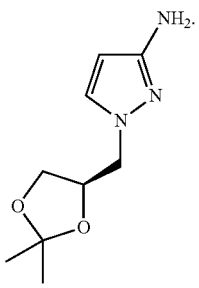
(Ia)

3. The process according to claim 1, wherein the compound of the formula (I) is 1-((R)2,2-dimethyl-[1,3]dioxolan-4-yl-methyl)-1H-pyrazol-3-ylamine 4. The process according to claim 1, wherein a) is performed with a carboxylating agent at a reaction temperature between 20 and 100° C.

5. The process according to claim 4, wherein the reaction is performed in a solvent that is tetrahydrofuran, acetic acid, water, iso-propyl acetate or ethyl acetate.

6. The process according to claim 4, wherein the carboxylating agent is acetic anhydride, acetyl chloride, benzoic anhydride, benzoyl chloride or pivaloyl chloride.

7. The process according to claim 4, wherein the reaction temperature is between 40 and 80° C.

8. The process according to claim 1, wherein b) is performed with an alkylation agent in an organic solvent with a base and a lithium salt additive at temperature of 70 to 150° C.

9. The process according to claim 8, wherein that the solvent used in b) is dimethylformamide, dimethylacetamide, N-methylpyrrolidinone or dimethylsulfoxide.

10. The process according to claim 8, wherein the base in b) is sodium, lithium or potassium salts of an alkoxide.

11. The process according to claim 8, wherein the lithium salt used in b) is lithium chloride, lithium bromide or lithium iodide.

12. The process according to claim 8, wherein in the alkylation agent in b) is

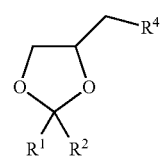

wherein
R$^4$ is chloro, bromo, iodo or —O—SO$_2$—R$^5$, wherein R$^5$ is C$_{1-6}$alkyl, phenyl or phenyl substituted by one to three substituents that are, independently, C$_{1-6}$alkyl, halogen or nitro.

13. The process according to claim 12, wherein the alkylation agent in b) is

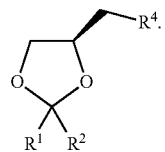

14. The process according to claim 8, wherein the reaction temperature step b) is between 90 and 110° C.

15. The process according to claim 1, wherein c) is performed in solvent with a base at a temperature of 40 to 100° C.

16. The process according to claim 15, wherein the solvent used in step c) is methanol, ethanol or water, or a mixture thereof.

17. The process according to claim 1, wherein the base used in c) is sodium hydroxide, lithium hydroxide or potassium hydroxide.

18. The process according to claim 15, wherein the reaction in c) is performed between 60 and 80° C.

19. A compound of formula (III);

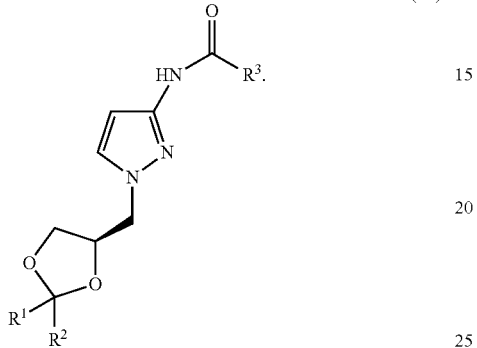

wherein $R^1$ is methyl, $R^2$ is methyl and $R^3$ is methyl.

* * * * *